(12) United States Patent
Pullen

(10) Patent No.: US 7,341,735 B2
(45) Date of Patent: *Mar. 11, 2008

(54) METHOD FOR USING AN ADJUVANT COMPOSITION WITH HERBICIDES, PESTICIDES, INSECTICIDES, OVICIDES AND FUNGICIDES TO CONTROL PESTS, INSECTS AND FUNGI

(75) Inventor: Erroll M. Pullen, Bantry Bay (ZA)

(73) Assignee: Oro Agri, Inc., Trophy Club, TX (US)

( * ) Notice: Subject to any disclaimer, the term of this patent is extended or adjusted under 35 U.S.C. 154(b) by 424 days.

This patent is subject to a terminal disclaimer.

(21) Appl. No.: 10/641,823

(22) Filed: Aug. 16, 2003

(65) Prior Publication Data

US 2004/0242428 A1   Dec. 2, 2004

Related U.S. Application Data

(63) Continuation-in-part of application No. 10/188,025, filed on Jul. 1, 2002.

(60) Provisional application No. 60/344,671, filed on Dec. 31, 2001.

(51) Int. Cl.
*A01N 25/00* (2006.01)
*A01N 25/08* (2006.01)
*A01N 25/24* (2006.01)

(52) U.S. Cl. .............. 424/405; 424/407; 424/409; 514/938; 514/975

(58) Field of Classification Search ............. None
See application file for complete search history.

(56) References Cited

U.S. PATENT DOCUMENTS

| | | | | |
|---|---|---|---|---|
| 3,584,119 A | * | 6/1971 | Langley | 424/657 |
| 5,744,137 A | * | 4/1998 | Stone | 424/184.1 |
| 5,753,593 A | * | 5/1998 | Pullen et al. | 504/150 |
| 6,258,369 B1 | * | 7/2001 | Pullen | 424/405 |
| 6,277,389 B1 | * | 8/2001 | Pullen | 424/405 |
| 6,455,086 B1 | * | 9/2002 | Trinh et al. | 426/321 |
| 6,500,445 B1 | * | 12/2002 | Pullen | 424/405 |

\* cited by examiner

*Primary Examiner*—David M. Naff
*Assistant Examiner*—Deborah K. Ware
(74) *Attorney, Agent, or Firm*—Milbank, Tweed, Hadley & McCloy LLP

(57) ABSTRACT

An adjuvant is disclosed for use with systemic herbicides, pesticides, insecticides, ovicides and fungicides for application on animals, birds, trees, plants, fruits and vegetables to enhance the action and effect of the systemic herbicides, pesticides, insecticides, ovicides and fungicides. The adjuvant comprises at least one surfactant and at least one high terpene containing natural oil.

1 Claim, No Drawings

METHOD FOR USING AN ADJUVANT COMPOSITION WITH HERBICIDES, PESTICIDES, INSECTICIDES, OVICIDES AND FUNGICIDES TO CONTROL PESTS, INSECTS AND FUNGI

CROSS REFERENCE

This is a continuation-in-part application of a co-pending application Ser. No. 10/188,025 filed Jul. 1, 2002 which claims benefit of 60/344,671, filed Dec. 31, 2001.

BACKGROUND OF THE INVENTION

1. Field of the Invention

An adjuvant for use with systemic herbicides, pesticides, insecticides, ovicides and fungicide on animals, birds, plants, trees, fruits and vegetables.

2. Description of the Prior Art

Various insects such as lice, ticks, mites and aphides attack untreated and unprotected trees and plants. Moreover, fungi left uncontrolled can damage and even destroy plants and trees including crops associated therewith.

In the past, various oils have been used to control insects and mites. Recently, however, renewed attention has focused on the use of oils as a natural substitute for traditional insecticides with attendant toxic and other dangerous side effects.

These oils include horticultural oils that are highly refined petroleum products than can be mixed with water for application for control of target insect and mite pests without deleterious effects. Modern horticultural oils do not include vegetable, fish or whale oils.

Horticultural spray oils are the low toxicity alternative to broad-spectrum insecticides. Since the mechanism of insect and mite control with spray oils is by suffocation and/or repellency of egg laying females, there is no requirement for the addition of toxic chemicals. These properties are a valuable and well-recognized component of the practice of integrated pest management where oil spraying is intrinsically linked to natural control of pests by predators and parasitoids. Horticultural spray oils are formulated on highly refined clear oil with a minimum of nonionic surfactant. Independent environmental impact studies have shown that D-C-TRON has no detrimental effect on the environment. Mammalian toxicity studies published in the American Journal of Industrial Medicine have shown that oils at this refinement level are non-toxic and non-carcinogenic.

Generally, oil sprays are safe to humans. These oil sprays have little, if any, negative effect on wildlife and non-target insects in the environment. Furthermore, oil sprays are less toxic due to the method by which they kill target pests. In particular, the thin film of oil covers the target insect or mite and plugs the spiracles or pores through which the pests or parasites breathe. The cause of death is primarily suffocation. Large, motile insects and animals that breathe by another method are not affected by these oils.

Another advantage of oil applications is the absence of objectionable odors. In addition, oils are relatively inexpensive and significantly less expensive than many insecticides.

Unfortunately, there are limitations to the use of oil treatments. For example, oils are only effective against those pests that are thoroughly coated by the spray solution. This usually means that only small, immobile or slow moving pests that are exposed on the surface of the plant or tree at the time of application will be controlled.

Since oil sprays only work by contracting and covering the target pest, thorough application is essential. Missed surface areas provide a safe refuge for the target pests.

U.S. Pat. No. 6,258,369 and U.S. Pat. No. 6,277,389 disclose a non-toxic aqueous pesticide for application on plants and animals comprising at least one surfactant and at least one high terpene containing natural oil. The pesticide is used to effectively control insects and parasites such as darkling beetles, lice, ticks, mites, flies, aphides, mosquitoes and chiggers found on plants and animals.

U.S. Pat. No. 5,693,344 shows a hazard-free method for controlling insects using a non-toxic composition in the form of a fragrance and crystalline particles which puncture directly through the exoskeleton of an insect. In operation, the particles work themselves between the insect's protective body plates and then puncture the exoskeleton permitting entry of the fragrance into the body of the insect. Once inside, the particles absorb up to four times their weight of the vital body fluids of the insect and the fragrance has a neural effect on the insect.

U.S. Pat. No. 5,143,939 shows a method of treating soil and agricultural crops for controlling worms and nematodes comprising a nonionic surfactant, namely an alkylox-ypolyethyleneoxyethanol used as the sole active ingredient to control fungus, mites, worms, termites, nematodes and other insects.

U.S. Pat. No. 4,379,168 relates to pesticides containing d-limonene as an insect-killing ingredient with surfactants or emulsifiers and water. The pesticide compositions are liquids designed for use as a dip to rid small animals of fleas and ticks, a spray to kill fleas and ticks on small animals and in the kennels of small animals; a spray to kill flies on small animals and in the kennels of small animals; and a spray or liquid to rid household areas of cockroaches and other insect pests.

U.S. Pat. No. 6,248,710 B1 discloses a water-soluble or water-dispersible material for deposition onto a fabric substrate during a treatment process comprising polysaccharide structure having at least one substituent benefit agent group and optionally, one or more other substituent groups. The polysaccharide structure has one or more regions with at least 3, preferably at least 4 consecutive unsubstituted saccharide rings.

SUMMARY OF THE INVENTION

The present invention relates to an adjuvant formulated for use on animals, birds, plants, trees, fruits and vegetables as an adjuvant in combination with systemic herbicides, pesticides, insecticides, ovicides and fungicide. The composition comprises at least one surfactant and at least one high terpene. The invention also includes the method of application of the composition.

High terpene containing natural oil as used herein means those natural oils having a terpene content of at least 50 percent. It is preferable that the high terpene natural oil contains at least 65 percent. Suitable high terpene containing natural oils includes oil from conifers such as citrus peel oils, preferably orange oil, grapefruit oil, lemon oil or pine oil. Of these, orange oil is preferred and cold pressed orange oil the most preferred. The preferred terpene content is from about 80 percent to about 90 percent and most preferred from about 85 percent to about 87 percent, all by weight.

The amount of high terpene containing natural oils in the composition depends upon the amount of terpenes in the specific oil used. Generally, the composition contains from about 2 percent by weight to about 8 percent by weight of high terpene containing natural oil, preferably about 5 percent by weight.

Anionic and nonionic surfactants are acceptable for use in the composition of the present invention. Anionic surfactants such as salts of fatty acids, alkyl sulphates, alkyl ether sulphonates and alkyl aryl sulphonates are preferred.

The composition may also contain preservatives, pH neutralizers and/or clarifiers or stabilizers. The balance of the composition is water.

In use, the adjuvant, when combined with systemic herbicides, pesticides, insecticides, ovicides and fungicides, is diluted and sprayed or misted on animals, birds, plants, trees, fruits or vegetables.

When so applied, the composition is effective as an adjuvant in enhancing the effect of systemic herbicides, insecticides, ovicides and fungicides that are applied to control various diseases, pests and insects including darkling beetles, lice, ticks, mites, flies, aphids, thrips, mealybugs, mosquitoes and chiggers.

The composition is also effective as an adjuvant in enhancing fungicides in controlling fungi. While not to be bound by theory, absorption of fungicide, once blended with the adjuvant, is increased both in speed as well as percentage absorbed.

Finally, the composition as an adjuvant enhances water penetration and absorption by the soil as well as decreases water logging. These better soil conditions lead to improved root and plant growth.

The invention accordingly comprises the features of construction, combination of elements, and arrangement of parts that will be exemplified in the construction hereinafter set forth, and the scope of the invention will be indicated in the claims.

DETAILED DESCRIPTION OF THE PREFERRED EMBODIMENT

The present invention relates to an adjuvant for use with systemic herbicides, pesticides, insecticides, ovicides and fungicides formulated for use with various animals, birds, trees, plants, fruits and vegetables. The composition comprises at least one surfactant and at least one high terpene containing oil to enhance the effectiveness of pesticides, insecticides, ovicides and fungicides in controlling pests, insects and fungi. The invention also includes the method of application of the composition. Furthermore, the composition may be used as an adjuvant with contact pesticides.

High terpene containing natural oil as used herein means those natural oils having a terpene content of at least about 50 percent. It is preferable that the high terpene natural oil contains at least about 65 percent. Suitable high terpene containing natural oils includes oil from conifers such as citrus peel oils, preferably orange oil, grapefruit oil, lemon oil or pine oil. Of these, orange oil is preferred and cold pressed orange oil the most preferred. The preferred terpene content is from about 80 percent to about 90 percent and most preferred from about 85 percent to about 87 percent, all by weight.

The amount of high terpene containing natural oils in the composition depends upon the amount of terpenes in the specific oil used. Generally, the composition contains from about 2 percent by weight to about 8 percent by weight of high terpene containing natural oil, preferably about 5 percent by weight.

Anionic and nonionic surfactants are acceptable for use in the composition of the present invention. Anionic surfactants such as salts of fatty acids, alkyl sulphates, alkyl ether sulphonates and alkyl aryl sulphonates are preferred. Examples of such surfactants may include from about 8 percent to about 12 percent sulfonic acid, preferably about 10 percent sulfonic acid; from about 5 percent to about 9 percent sodium laurel sulfate, preferably about 6.8 percent sodium laurel sulfate; from about 6 percent to about 10 percent alcohol ethoxylate, preferably about 8.2 percent alcohol ethoxylate; and from about 1 percent to about 3 percent olefin sulfonate, preferably about 1.7 olefin sulfonate, all by weight.

Generally, the composition contains from about 20 percent to about 34 percent surfactant(s), preferably from about 25 percent to about 30 percent surfactant(s) and most preferably about 26.7 percent surfactant(s), all by weight.

The composition may also include butylated hydroxytoluene, p-Hydroxybenzoic acid and/or sodium tetraborate decahydrate. The range of butylated hydroxytoluene is from about 0.05 percent to about 0.15 percent and preferably about 0.10 percent, all by weight. The range of sodium tetraborate decahydrate is from about 0.89 percent to about 1.09 percent and preferably about 0.99 percent, all by weight. The range of p-Hydroxybenzoic acid is from about 0.25 percent to about 0.35 percent and preferably about 0.30 percent, all by weight. Generally, the composition contains from about 1.39 percent to about 1.89 percent preservative(s), preferably about 1.64 percent preservative(s), all by weight.

In addition, a bactericide is from about 0.05 percent to about 0.15 percent and preferably about 0.10 percent, all by weight may be added.

Caustic crystals such as sodium hydroxide may be added in an amount of from about 1.25 percent to about 1.37 percent by weight to neutralize the composition to a pH of from about 7.75 to about 9.

A clarifier or stabilizer such as urea may be added in an amount of from about 0.59 percent to about 0.99 percent and preferably about 0.79 percent, all by weight.

The balance of the composition is made up by water.

The preferred composition comprises about 5 percent cold pressed orange oil, about 6.8 percent sodium lauryl sulfate, about 8.2 percent of alcohol ethoxylate, about 1.7 percent sodium olefin sulfonate, about 10 percent dodecylbenzene sulphonic acid, about 0.1 percent antioxidant such as butylate hydroxytoluene, about 0.30 percent preservative such as p-Hydroxybenzoic acid, about 0.1 percent bactericide, about 0.99 percent fungicide such as sodium tetraborate decahydrate, about 0.79 percent clarifier such as urea and about 1.31 percent neutralizer such as sodium hydroxide with the balance a diluent such as water, all by weight.

In use, the adjuvant composition is combined with a herbicide, pesticide, insecticide, ovicide or fungicide effective as either a contact or systemic herbicide, pesticide, insecticide, ovicide or fungicide. An effective range for the adjuvant composition is from about ½ part to about 8 parts adjuvant to 1000 parts herbicide, pesticide, insecticide, ovicide or fungicide and water. The preferred range for the adjuvant composition is from about 1½ parts to about 4 parts adjuvant composition to 1000 parts herbicide, pesticide, insecticide, ovicide, fungicide. The preferred concentration of adjuvant concentration is about 2 parts adjuvant composition to 1000 parts herbicide, pesticide, insecticide, ovicide or fungicide.

The combined adjuvant composition and herbicide, pesticide, insecticide, ovicide or fungicide is applied to plants or row crops such as most vegetables at an application rate of about five (5) liters or less per acre.

The combined adjuvant composition and herbicide, pesticide, insecticide, ovicide or fungicide is applied to trees or orchards at an application rate of about eight (8) liters or less per acre.

While the invention has been described above with respect to certain particular embodiments thereof, numerous other forms and modifications will be apparent to those skilled in the art. The appended claims and the invention generally should be construed as covering all such obvious forms and modifications that are within the true spirit and scope of the invention.

It will thus be seen that the objects set forth above, among those made apparent from the preceding description are efficiently attained and since certain changes may be made in the above construction without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A method of enhancing control of pests, insects and fungi on animals, birds, trees, plants, fruits and vegetables by applying a pesticide, insecticide, and/or fungicide in combination with an adjuvant composition to potentiate the pesticide, insecticide, and/or fungicide, said adjuvant composition comprising about 5 percent cold pressed orange oil, about 6.8 percent sodium lauryl sulfate, about 8.2 percent of alcohol ethoxylate, about 1.7 percent sodium olefin sulfonate, about 10 percent dodecylbenzene sulphonic acid and about 0.99 percent sodium tetraborate decahydrate with the balance water, all by weight, said adjuvant composition comprising about 0.2 percent of the combination of a pesticide, insecticide and/or fungicide and said adjuvant composition.

* * * * *